US00PP15791P2

(12) United States Plant Patent
Bennerup

(10) Patent No.: US PP15,791 P2
(45) Date of Patent: Jun. 7, 2005

(54) ***SANGUISORBA* PLANT NAMED 'DALI MARBLE'**

(50) Latin Name: *Sanguisorba menziesii*
Varietal Denomination: Dali Marble

(75) Inventor: Pierre Robert Bennerup, Berlin, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 61 days.

(21) Appl. No.: 10/774,621

(22) Filed: Feb. 9, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Penny J. Aguirre

(57) ABSTRACT

The new cultivar, *Sanguisorba menziesii* 'Dali Marble', characterized by its variegated foliage; exhibiting green centers with white margins and red-purple flower spikes in late summer and fall.

2 Drawing Sheets

Botanical classification: *Sanguisorba menziesii.*
Variety denomination: 'Dali Marble'.

BACKGROUND OF THE INVENTION

The present invention relates to a new and distinct cultivar of *Sanguisorba menziesii* and will be referred to hereafter by its cultivar name, 'Dali Marble'. 'Dali Marble' represents a new Burnet, an herbaceous perennial grown for landscape use.

The inventor discovered and selected the new cultivar, 'Dali Marble', as a naturally occurring mutant seedling in the fall of 1997 in Kensington, Conn. The new cultivar was derived from seeds of *Sanguisorba menziesii* that the inventor collected in Yunnan province in Southwest China in 1996 and sowed in his nursery in the fall of 1996. No other species or cultivars of *Sanguisorba* were growing in the area and based on the overall botanical characteristics, both parents are presumed to be *Sanguisorba menziesii.*

'Dali Marble' was selected for the unique characteristic of exhibiting variegated foliage. The foliage of 'Dali Marble' is green with a white margin. This characteristic makes this new cultivar unique to the species and unlike any other known cultivars of *Sanguisorba menziesii* known to the inventor.

Asexual reproduction of the new cultivar was first accomplished by terminal stem cuttings Kensington, Conn. in April of 1998 by the inventor. The characteristics of this cultivar have been determined to be stable and are reproduced true to type in successive generations.

SUMMARY OF THE INVENTION

The following traits have been repeatedly observed and represent the characteristics of the new cultivar as grown outdoors in Kensington, Conn. These attributes in combination distinguish 'Dali Marble' from other varieties in known to the inventor.

1. Foliage is variegated with medium green centers and white margins.
2. Plants reach about 1.2 m in height and about 30 cm in width in a growing season when grown from a single stem division.

3. Terminal red-purple spikes of tightly packed flowers appear in late August through early October in Kensington, Conn.
4. Tolerant to a range of growing conditions, growing well in full sun to light shade in any soils with sufficient moisture.

BRIEF DESCRIPTION OF THE DRAWING

The accompanying colored photographs illustrate the overall appearance and distinct characteristics of the new *Sanguisorba.*

The photograph on the first sheet shows the plant habit and foliage in mid August. 'Dali Marble' is in the center of the photograph.

The photograph on the top of the second sheet comprises of a close-up view of the foliage and is indicative of the variegation pattern of 'Dali Marble'.

The photograph on the bottom of the second sheet depicts a one-year plant in bloom in early October in Kensington, Conn. The colors in the photographs are as close as possible with the digital photography techniques available, the color values cited in the detailed botanical description accurately describe the colors of the new *Sanguisorba.*

DETAILED BOTANICAL DESCRIPTION

The following is a detailed description of the new cultivar as grown outdoors in moist garden soil in full sun. The plants used for the descriptions and photographs were grown for one year from a 32-cell liner. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Dali Marble' is a cultivar of *Sanguisorba menziesii.*

*Common name.*—Dali Marble Burnet.

*Parentage.*—Naturally occurring mutant seedling of *Sanguisorba menziesii.*

*Blooming period.*—Late August through early October in Kensington, Conn.

*Plant habit.*—Herbaceous perennial. Clump-forming, upright and arching outward.

*Height and spread.*—About 1.2 m (about 3.5' to 4') in height, about 30 cm (about 12") in width at base.

*Hardiness.*—Zone 4.

*Culture.*—Any sufficiently moist soils in full sun to partial shade.

*Diseases and pests.*—No susceptibility or resistance to diseases or pests known to effect *Sanguisorba menziesii* has been observed for 'Dali Marble'.

*Root description.*—Fibrous, well-branched root from stout rhizomes.

Growth and propagation:

*Propagation.*—Terminal stem cutting from vegetative shoots (preferred) or division of lateral off shoots.

*Root initiation.*—Develop in 7 to 10 days under greenhouse conditions under mist at 21° C. to 23° C.

*Time required for root development.*—1 month to fully develop a 32-cell liner.

*Growth rate.*—Moderate growth rate, develops 10 to 12 shoots in the garden from a 32-cell liner or single stem division.

Stem description:

*Shape.*—Round.

*Stem color.*—Ranges from 144A to 144B.

*Stem size.*—Up to about 6 mm in diameter and about 1.2 m in flowering stems (including peduncle), up to about 4 mm in diameter and about 60 cm on lateral stems.

*Stem surface.*—Glabrous.

*Internode length.*—3.5 to 5.0 cm in length.

*Stipules.*—Leafy, fan-shaped, on very short petiole, typically 2 per node, 2 cm in length, 1 cm in width, upper color 137A, lower color 138A, few are variegated.

*Branching.*—Basal branches only, inner branches are flowering, lateral branches remain vegetative, 3 to 4 flowering stems and 4–7 lateral branches on a one-year plant.

Foliage description:

*Leaf shape.*—Ovate to oblong.

*Leaf division.*—Imparipinnate, typically composed of 7 to 11 leaflets (simple division).

*Leaf base.*—Cordate, often with two uneven sides.

*Leaf apex.*—Rounded.

*Leaf fragrance.*—None.

*Leaf venation.*—Upper and lower surface; conspicuous, near base 144B, midrib and other veins same as leaf color.

*Leaf margins.*—Serrate, typically about 30 serrations per leaflet on mature leaves.

*Leaf arrangement.*—Alternate, individual leaflets are opposite.

*Leaf attachment.*—Sessile (leaves), petiolulate (leaflets).

*Rachis size.*—Up to about 15 cm in length, 1 to 2 mm in width.

*Petiolule size.*—About 0.6 to 2 cm in length, 1 to 1.5 mm in width.

*Rachis and petiolule color.*—Ranges from 144B to 144A.

*Leaf surface.*—Upper; glabrous (slightly glaucous). Lower; glaucous.

*Leaf size.*—Leafs on lateral shoots; up to about 20 cm in length, 15 cm in width. Leaflets on lateral shoots; up to about 9 cm in length (8 typical), up to about 6 cm in width (5 typical). Leafs on blooming branches; up to 15 cm in length, up to 4 cm in width, leaf size decrease towards apex.

*Immature leaf color.*—Upper surface; color between 137B and 143A, margins 4C to 4B. Lower surface; 138A to 191A, margin color same as upper surface.

*Mature leaf color.*—Upper surface; 189A, margin 155D to 4D. Lower surface; 191A, margin 155D to 4D, intermediate area 189A or 190B (if present).

*Description of variegation pattern.*—Variegation is essentially limited to margins, extending 1 to 3 mm from edge, occasionally extending towards leaf center in an irregular pattern rarely exceeding ⅛ of leaf surface. Variegation is effectively white margins on green centers.

Inflorescence description:

*Type.*—Terminal spikes of numerous, densely packed flowers in elongated ovoid to oblong shaped inflorescence, determinate.

*Arrangement.*—3 to 5 spikes per flowering stem, arranged alternately in cyme-like pattern on sparsely leaves peduncles.

*Fragrance.*—None.

*Lastingness.*—About 7 days, persistent.

*Quantity.*—About 100 flowers per spike, about 7 to 15 flowers per plant.

*Aspect.*—Terminal spikes held upward, lateral spikes held at 45° from stem.

*Size.*—Terminal; up to about 3 cm in length, 1.2 cm in width. Lateral; up to 1.5 in length, 1.1 cm in width.

*Color.*—Overall effect is red-purple 64A.

*Peduncle.*—10 to 15 cm in length, 1 to 1.5 mm in width, color 144A.

*Bud description.*—Arranged in oval-shaped clusters, up to 1.5 cm in length and 9 mm in width when color appears, emerge 145C turning to 144C, becoming tinged with 64B prior to opening.

*Flower type.*—Apetalous, composed of 4-parted calyx with tube opening to spreading petaloid lobes in rotate-like form, sessile.

*Flower size.*—About 4 mm in diameter, 3 mm in height.

*Flower color.*—See sepal description.

*Petals.*—Absent.

*Calyx description.*—4-angled, ovoid with tube with separating and spreading petaloid, ovate-shaped lobes.

*Sepal color.*—Tube; green 144C with markings of dark red-purple. Petaloid lobes; N74C with green center stripe, 144C.

*Sepal appearance.*—Tube; hairy. Petaloid lobes; glabrous and translucent.

*Sepal size.*—Tube; 1 mm in length, 1.5 mm in width. Petaloid lobes; 2 mm in length, 1.5 mm in width.

*Flower bracts.*—Very fine, 0.5 mm in length, 0.25 mm in width, long fine hairs, 2 per flower.

Reproductive organs:

*Gynoecium.*—1 Pistil, stigma is pencillate, ovary is single celled and superior.

*Androcoecium.*—4 stamens, pollen is not visible.

*Fruit.*—Not observed under conditions tested, a coriaceous achene would most likely form when grown in more southern locations.

It is claimed:

1. A new and distinct cultivar of *Sanguisorba* plant named 'Dali Marble' as herein illustrated and described.

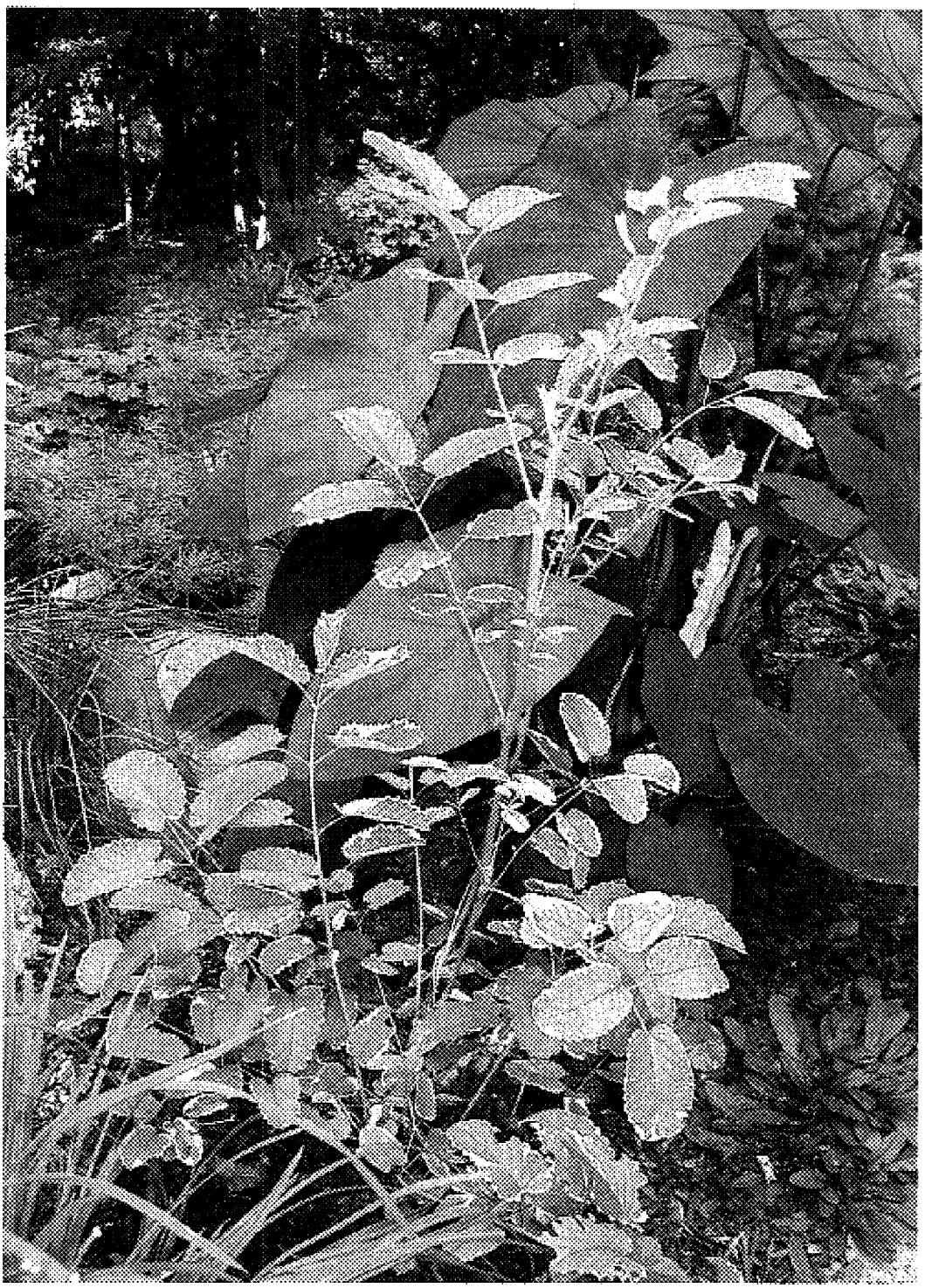

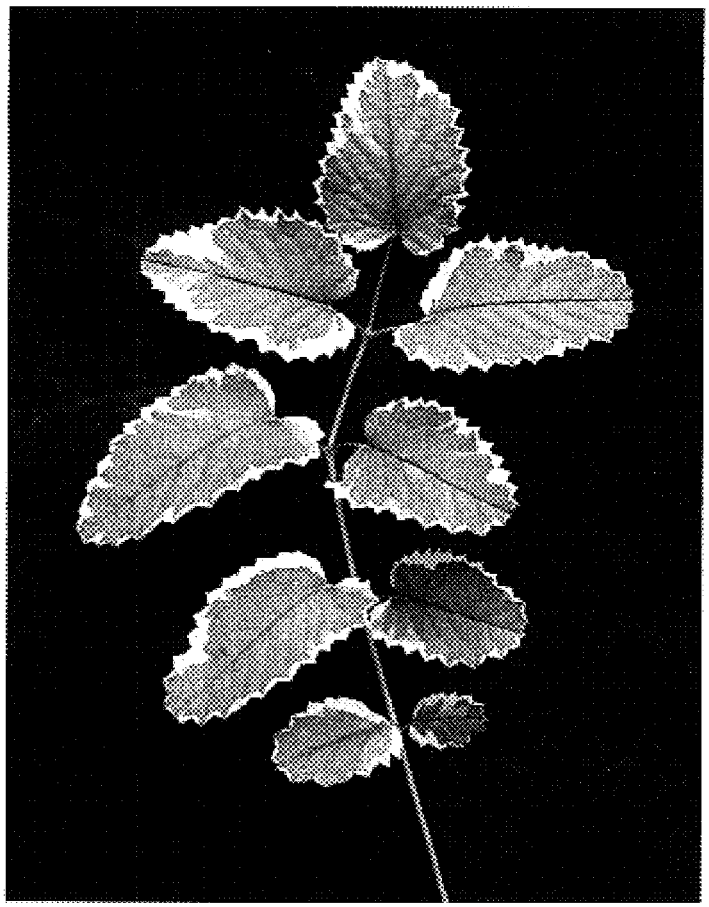
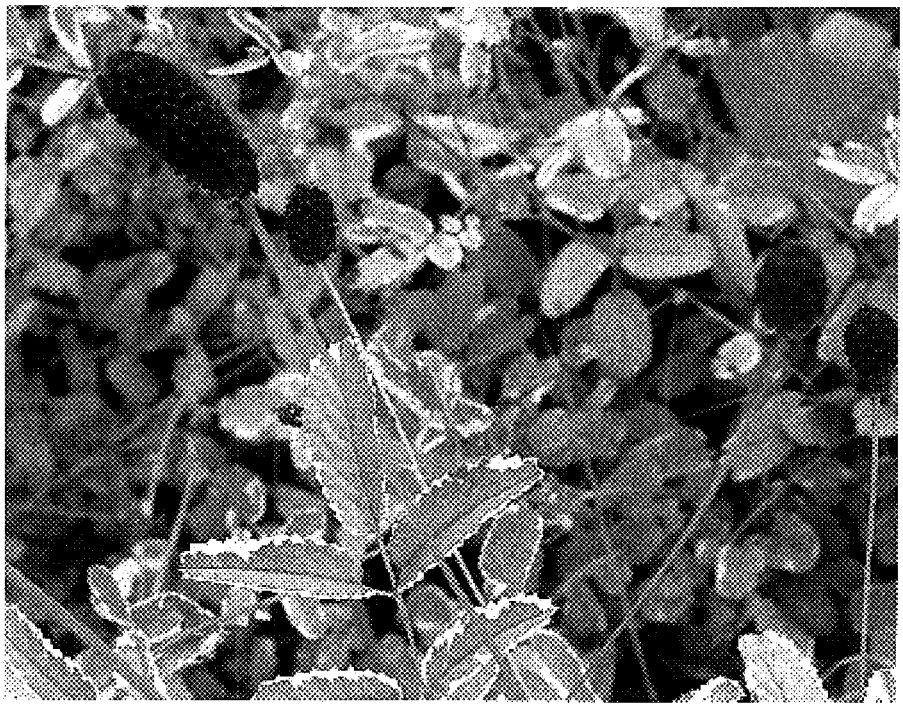

* * * * *